United States Patent [19]

Platt

[11] Patent Number: 5,681,923

[45] Date of Patent: Oct. 28, 1997

[54] TUMOR DERIVED CARBOHYDRATE BINDING PROTEIN

[76] Inventor: David Platt, One Kendall Sq., Bldg. 300, Cambridge, Mass. 02139-9645

[21] Appl. No.: 540,202

[22] Filed: Oct. 6, 1995

[51] Int. Cl.[6] .................................................. C07K 14/47
[52] U.S. Cl. ........................................................ 530/300
[58] Field of Search .............................................. 530/300

[56] References Cited

U.S. PATENT DOCUMENTS 5,260,434  11/1993  Liu .

OTHER PUBLICATIONS

Raz, Cancer Research 51:2173–2178, 1991.
Oda, Gene 99:279–283, 1991.
Robertson, Biochemistry 29:8093–8100, 1990.
"Low Colony Formation I Vivo and in Culture as Exhibited by Metastatic Malanoma Cells Selected for reduced Homotypic Aggregation", Cancer Research 43:12088–2093, Lotan et al. (1983).
"A Lectin–Binding Protease–Resistant Mycobacteria Ligand Specifically Activates Vγ9+ Human γδ T Cells", The Journal of Immunology, 148:575, Pfeffer et al. (1992).

*Primary Examiner*—Lila Feisee
*Assistant Examiner*—Nancy A. Johnson
*Attorney, Agent, or Firm*—Gifford, Krass, Groh, Sprinkle, Patmore, Anderson & Citkowski, P.C.

[57] ABSTRACT

The active, galactose binding site of proteins associated with metastatic tumor cells has been identified and sequenced (SEQ. ID. NO:1). The polypeptide comprising the active site may be used as an immunotherapeutic agent. Identification of the site makes possible an in vivo diagnostic assay for metastatic cells as well as therapeutic methodologies and materials.

2 Claims, 2 Drawing Sheets

TUMOR DERIVED CARBOHYDRATE BINDING PROTEIN

FIELD OF THE INVENTION

This invention relates to carbohydrate binding proteins. More specifically, the invention relates to a group of proteins referred to as lectins, which are associated with tumor cells and which have a binding affinity for carbohydrates such as galactose. Most specifically, the invention relates to a particular amino acid sequence in the protein which is responsible for its galactose binding activity. In particular embodiments, the present invention includes assays for the presence of tumor cells as well as therapies for inhibiting metastasis of tumor cells.

BACKGROUND OF THE INVENTION

A major thrust in metastasis research has been the search for cellular genes and other epigenetic factors which control the metastatic cascade. It has been determined that there is a close correlation between tumor cell surface receptors and metastasis of those cells. This research has led to the supposition that cellular interactions are influenced by cell surface components; however, a detailed structural analysis of such cellular components has not heretofore been undertaken.

In accord with the present invention, it has been found that particular tumor cells include a class of proteins termed lectins on their surface, and these lectins bind to galactose. Accordingly, within the context of this disclosure, such lectins will be collectively referred to as carbohydrate binding proteins (CBP). Tumor progression can be delineated as either suppressed or enhanced expression of a relatively limited number of cell proteins, and the CBPs have been found to increase in number as a tumor progresses to metastasis. Consequently, the CBPs play a pivotal role in malignant biochemical transformation. It is believed that CBP may mediate the interaction between adjacent cells and cell matrix recognition by binding complementary glycoconjugates.

The amino acid sequence of a number of CBPs has previously been determined; however, the precise structure of the active portion of CBPs responsible for the galactose binding was heretofore unknown. In general, it has been found that the carbohydrate binding protein isolated from different tissues by affinity chromatography appears to constitute two different classes of peptides. One class of peptides has a molecular weight of about 14,000 dalton. The other class has a molecular weight ranging between 20,000–35,000 daltons. It has also been found that CBPs obtained from different species of animals often show immunological cross activity, suggesting structural similarities. Galactose binding proteins of approximately 14,000 and 34,000 daltons have been extracted and cloned from different tissues, and from various species. These materials have been sequenced and the homology range is from 40–80%. Therefore, it will be appreciated that data developed in animal models, such as the mouse or rat, is highly applicable to another species including humans.

It has been found that a number of different tumor cells contain CBPs that are very similar to those isolated from normal cells having sugar binding specificity. Further studies have shown that neoplastic transformation is associated with the concomitant expression of an additional, unique CBP species having a molecular weight of approximately 34 kilodalton designated as L-34; see, Lotan, R and Raz A. *Cancer research* 43:2088 (1983).

Other families of carbohydrate-binding proteins that share common binding specificity for sugars such as galactose exist, despite the fact that such proteins are very diverse in structure and function. Included are a group of 14 kilodalton galactoside binding lectins, a 64 kilodalton component of the elastin receptor, the 55 kilodalton ectosialyltransfarese of Hodgkins disease, the 43 kilodalton human actin-binding brain lectin, the 50 kilodalton rat testis galactosyl receptor, the murine and human tumor associated 34 kilodalton lectin, the 35 kilodalton fibroblast carbohydrate-binding protein, the IgE-binding protein, the 32 kilodalton macrophage nonintegrin laminin-binding lectin and the rat, mouse and human 29 kilodalton galactoside-binding lectin. All of these diverse polypeptides have been found to share significant homology and are designated carbohydrate-binding proteins within the context of this disclosure.

Based upon studies of the various tumor cells it has been found that CBPs play a role in cellular interactions in vivo. These reactions are important for the formation of emboli and the arrest of circulating tumor cells leading to the development of metastatic lesions.

In accord with the present invention, the active site on the carbohydrate-binding protein responsible for galactose affinity has been identified. Furthermore, it has been found that this particular amino acid sequence is highly homologous throughout a number of species. For example, the site approaches 90% homology in mouse and human tissues. For this reason, results obtained from studies in mice are highly predictive of human results. In accord with a further aspect of the present invention, there is provided a highly sensitive blood test for the presence of potentially metastatic tumor cells, which is based upon detecting the presence of the particular galactose-binding site. The present invention also makes possible, and includes therapeutic methods for inhibiting metastases, based upon the properties of the galactose receptor. These and other advantages of the present invention will be apparent from the drawings, discussion and description which follow.

Listing of Amino Acids

In accord with the conventions codified in 37 C.F.R. 1.821, the abbreviations used for amino acids in the following disclosure and claims shall be:

Ala—alanine
Arg—arginine
Asn—asparagine
Asp—aspartic acid
Cys—cysteine
Glu—glutamic acid
Gln—glutamine
Gly—glycine
His—histidine
Ile—isoleucine
Leu—leucine
Lys—lysine
Met—methionine
Phe—phenylalanine
Pro—proline
Ser—serine
Thr—threonine
Trp—tryptophan
Trp—tyrosine
Val—valine

BRIEF DESCRIPTION OF THE INVENTION

There is disclosed herein a galactose-specific, carbohydrate binding protein. The protein includes the amino acid sequence (SEQ ID NO:1) consisting essentially of:

Ile, Val, Cys, Ash, Thr, Lys, Leu, His, Asn, Asn, Trp, Gly, Arg, Glu, Glu, Arg, Gln, Ser, Val, Phe, Pro, Phe, Glu, Ser, Gly.

In a still further embodiment, the protein includes the longer amino acid sequence (SEQ ID NO:2):

His, Phe, Asn, Pro, Arg, Phe, Asn, Glu, Asn, Asn, Arg, Arg, Val, Ile, Val, Cys, Asn, Thr, Lys, Leu, His, Asn, Asn, Trp, Gly, Arg, Glu, Glu Arg, Gln, Ser, Val, Phe, Pro, Phe, Glu, Ser, Gly.

In another embodiment, the method includes an immunotherapeutic method for generating antibodies in animals to cells which include a galactose specific carbohydrate binding protein. The method includes the steps of providing a polypeptide which includes the amino acid sequence: (SEQ ID NO:1)

Ile, Val, Cys, Asn, Thr, Lys, Leu, His, Asn, Asn, Trp, Gly, Arg, Glu, Glu, Arg, Gln, Ser, Val, Phe, Pro, Phe, Glu, Ser, Gly;

injecting the polypeptide into an animal so that an immune response occurs wherein the animal generates antibodies to the peptide. In some embodiments, adjuvants may be employed to increase antibody production. In other embodiments, antibodies may be raised in one animal and subsequently transferred to another for therapy.

In accord with another embodiment of the present invention, there is provided an assay method for determining the presence of metastatic cells in an animal's bloodstream. The method includes the steps of providing a support member having a binding affinity for a carbohydrate binding protein which includes the amino acid sequence: (SEQ ID NO:1)

Ile, Val, Cys, Asn, Thr, Lys, Leu, His, Asn, Asn, Trp, Gly, Arg, Glu, Glu, Arg, Gln, Ser, Val, Phe, Pro, Phe, Glu, Ser, Gly;

contacting the support member with a fluid sample from the animal, maintaining the fluid sample in contact with the support member so that any of said carbohydrate binding protein present in the fluid sample will bind to the support; and detecting the bound protein, whereby the presence of the protein is indicative of the presence of metastatic cells in the animal. In one particular embodiment, the support member includes pectin adhered thereto. The step of detecting the bound protein may comprise contacting the bound protein with an antibody having affinity for the protein and subsequently detecting that protein. Also included is an assay kit for carrying out the analysis.

In another embodiment, the present invention includes a therapeutic method for inhibiting metastasis of a tumor cell of the type expressing a galactose binding protein and the surface thereof. The method comprises contacting the cell with the therapeutic agent which comprises galactose bound to a polymer. The polymer is preferably of a molecular weight in excess of 10 kilodaltons. The galactose may be part of a polysaccharide chain bound to the polymer.

BRIEF DESCRIPTION OF THE DRAWINGS

FIG. 1 is a schematic depiction of a portion of a CBP including the amino acid sequence of the present invention which constitutes the galactose binding site the;

DETAILED DESCRIPTION OF THE INVENTION

The present invention identifies, and is directed to a particular amino acid sequence which provides the galactose binding site of CBPs. A particular sequence (SEQ ID NO:2), in accord with the present invention, comprises the amino acids:

His, Phe, Asn, Pro, Arg, Phe, Asn, Glu, Asn, Asn, Arg, Arg, Val, Ile, Val, Cys, Asn, Thr, Lys, Leu, His, Asn, Asn, Trp, Gly, Arg, Glu, Glu, Arg, Gln, Ser, Val, Phe, Pro, Phe, Glu, Ser, Gly.

The amino acids are joined by peptide linkages, and it is to be understood that when expressed in a cell, the foregoing sequence will generally be a part of a longer chain of amino acids forming a protein. As will be discussed further hereinbelow, this active site need not occur in a larger protein, and in accord with the present invention, it will have a number of utilities even as a relatively short polypeptide. It has further been found in accord with the present invention that the most active portion of the aforementioned sequence (SEQ ID NO:2) comprises the amino acid chain (SEQ ID NO:1):

Ile, Val, Cys, Asn, Thr, Lys, Leu, His, Asn, Asn, Trp, Gly, Arg, Glu, Glu, Arg, Gln, Ser, Val, Phe, Pro, Phe, Glu, Ser, Gly.

It has been found that the active site of CBPs is highly homologous throughout a number of species, and throughout a number of different tissues in a particular species. As understood in the art, homologous amino acid sequences comprise those sequences in which there is substantial similarity in corresponding amino acids. For example, the 38 amino acid sequence (SEQ ID NO:2) listed above was derived from human HeLa-s3 tumor cells and this sequence has been found to be 96.4% homologous with a corresponding sequence of a galactose specific lectin from rats (rattus norvegicus) and 96.0% homologous with a galactose specific lectin from mice (mus musculus). Therefore, it will be appreciated that, in accord with the present invention, the amino acid sequence comprising the active portion of the CBP will include the structures listed above, as well as various homologous structures, generally those having a degree of homology of 80% or more. As is known in the art, various amino acids, such as Glu and Gln may in some instances be substituted for one another and such non-essential substitutions are all within the scope of the present invention.

Figure 1:
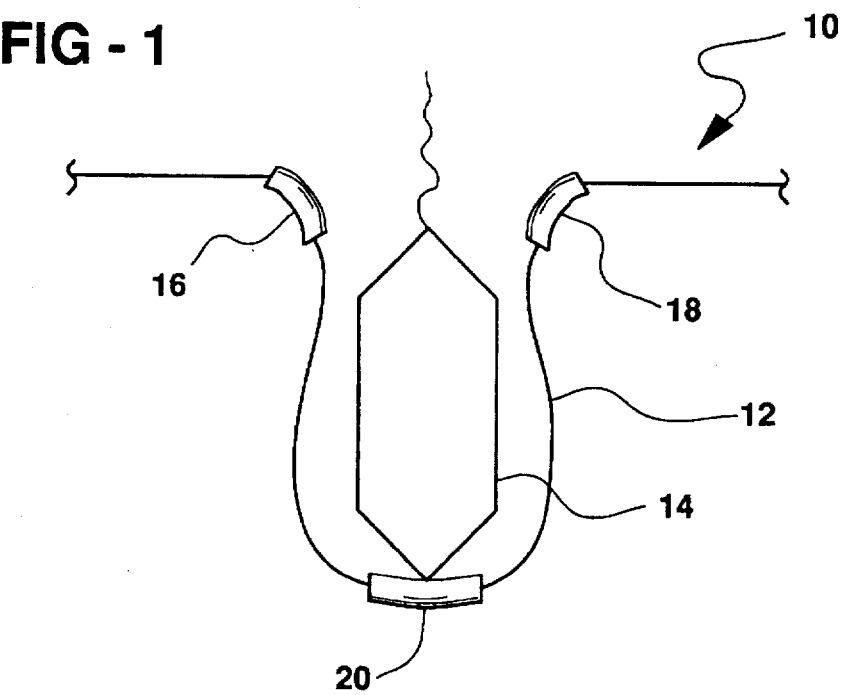

Referring now to FIG. 1, there is shown a portion of the protein chain of a CBP 10, illustrating the active site 12 of the present invention. As illustrated, the active site is shown as a pocket, or open loop in the protein chain, and it is to be understood that this is merely a schematic, two dimensional illustration. The active site, constituted by the homologous series of amino acids may actually assume more complex three dimensional configurations. In general, the active site will form a pocket in which the galactose, shown here schematically at 14, is retained by a combination of steric and electronic interactions. It is also to be understood that while the schematic depiction of FIG. 1 shows the galactose 14 as a simple sugar, the galactose may also comprise a portion of a polysaccharide structure. It is speculated that the galactose binding activity of the amino acid sequence may be dependent, to a large degree, upon some particular subportions of the chain. For example, a first portion, shown schematically by block 16, and a second portion, shown schematically by block 18 may possibly form the start and finish of the most active portion of the receptor, and as such may be responsible for establishing and maintaining the geometry of the opening to the receptor and/or may play a role associated with the entry and exit of the galactose from the receptor 12. A third sequence 20, at a position on the chain intermediate the first 16 and second 18 sequence may also be responsible for orienting and maintaining the galactose in the receptor. It is believed that the first sequence 16 includes the amino acids: (SEQ ID NO:3) Ile, Val, Cys, Asn, Thr, Lys. The second sequence 18 includes the amino acids: (SEQ ID NO:4) Val, Phe, Pro, Phe and the third sequence 20 includes the amino acids: (SEQ ID NO:5) Trp, Gly, Arg, Glu, Glu, Arg.

In accord with another feature of the present invention, there is provided an assay procedure for detecting metastatic cells in an animal. As described above, CBPs which include a specific galactose binding site are expressed by various tumors. It has been found that these CBPs are released from the metastatic cells, by a presently unknown mechanism, into the blood serum of patients, and this forms the basis for the assay.

The assay is accomplished by contacting a fluid sample, typically serum, with a support member such as a test plate which has a binding affinity for the CBPs. The support member thus retains the CBPs, and in a subsequent step they are detected.

The support member typically comprises a solid plate, a porous membrane or a volume of beads which are made of, or coated with a material to which the receptor of the present invention binds. This material generally comprises a carbohydrate based material which expresses galactose and/or galactose containing polysaccharides thereupon. One preferred binding material comprises pectin, and one particularly preferred type of pectin comprises a modified citrus pectin which is prepared in accord with the teachings in U.S. patent application Ser. No. 08/024,487, the disclosure of which is incorporated herein by reference. The support can be in the form of a microtitre plate or various other structures well known in the art. The plate may be coated with pectin by dissolving the pectin in a phosphate buffer and cross-linking it with glutaraldehyde, as will be described in detail hereinbelow. If a microtitre plate is used the sample can be pipetted into a well of the plate wherein the sample is exposed to a surface of the well having the binding material adhered thereto. Typically, the sample is maintained in contact with the well for a period of time to facilitate optimum binding. While there is a wide variation of time and temperature conditions, it has generally been found that incubation may be effectively accomplished at 4° C. for 24 hours. Once incubation is complete, the CBP in the sample will be bound to the plate.

The plate is then washed and a second fluid sample containing an antibody to the CBP is pipetted into the well. Most preferably, the antibody is an antibody having specific affinity for the CBP. In many instances, monoclonal antibodies are particularly preferred since they are highly specific and eliminate cross reactivity and false indications. Techniques for the preparation of monoclonal antibodies are well known in the art. In a final step, the bound antibodies are detected. Detection may be carried out by contacting the plate with a third material which binds to the antibodies and which also includes a tag or label for enabling detection of the bound antibody. The label may be a radioisotope label, a fluorophore or a chemically reactive tag such as a component of the biotin-avidin system. In the biotin-avidin assay a biotinylated antibody against the galactose binding site and a labelled streptavdin conjugate are used.

It will be appreciated that there are a number of modifications to this system which will be readily apparent to those of skill in the immunological arts. For example, instead of a plate, the solid support may comprise beads or microspheres of a material such as latex, coated with pectin or another such material which binds to the CBP, and the occurrence of binding may be detected by agglomeration or precipitation of the particles. In other instances, the support may be coated with an antibody which has a binding affinity for the noted amino acid sequence.

The assay of the present invention will be better illustrated by the experiments which follow.

EXPERIMENTAL EVIDENCE

Materials and Methods

1. Cell and Culture Conditions

High-metastatic murine cell variants of B16 melanoma, UV-2237 angiosarcoma and the human HeLa-S3 tumor systems were used.

The cells were grown as monolayers on plastic in Dulbecco's modified Eagle's minimal essential medium, supplemented with 10% heat-inactivated fetal bovine serum (FBS), nonessential amino acids, L-glutaine, vitamins and antibiotics (CMEM). The cells were maintained at 37° C. in a humidified atmosphere of 7% CO2 93% air. Cells were harvested by overlaying the monolayers with 2 mM EDTA in Ca++ and Mg++ free phosphate buffered saline, pH 7.2 calcium magnesium free PBS (CMF-PBS). Cell viability was assessed by trypan blue exclusion and only single cell suspensions with viability greater than 95% were used in the studies. To ensure reproductivity, the experiments were performed with cultures grown for no longer than six weeks after recovery from frozen stocks of low passage cells.

2. Purification of endogenous CBPs by affinity chromatography

Cells were extracted by homogenization in a solution containing 4 mM beta-Mercaptoethanol and 2 mM EDTA and 1 mM PMSF in Calcium Magnesium free phosphate buffer solution (CMF/PBS) ph 7.2 and 0.3M lactose. A 100,000× g supernatant fraction of the homogenate was dialyzed against MEPBS and applied onto an affinity column consisting of lactose that is bound covalently to Affi-Gel 10 (Pierce Chemical Co. ). After washing out the unbound material with MEPBS, the bound material was eluted with 0.3M lactose in MEPBS. The fraction was separated on Sepharose G-50 with MEPBS and the presence of CBP was determined in each fraction by SDS polyacrylamide gel electrophoresis (SDS-PAGE) and immunoblot. The fractions were pooled and used for amino acid analysis and the generation of monoclonal antibodies against the galactose binding site, (anti CBP antibodies).

Cells and protein from the G-50 separation were lyzed in 0.5 NP-40, 1 mM EDTA, and 1 mM PMSF in PBS, separated by electrophoresis on reducing 12.5% SDS-PEG, and electrotransferred to nitrocellulose filters. The filters were quenched overnight in PBS containing 15% skim milk (1% fat) and $NAN_3$. Then the filters were incubated with the chosen anti-CBP antibodies in the quench solution. The filters were washed five times for 15 minutes and then incubated for one hour in the quench solution with $^{125}$I-goat anti-rabbit (IgGs). The filters were washed twice for 15 minutes with the quench solution and twice more for 15 minutes with the quench solution containing 0.1% Tween- 20, dried with paper towel, wrapped in Saran-Wrap and exposed at −70° C. to x-ray film.

4. Antibodies

Monoclonal antibodies were generated against the amino acid sequence: (SEQ ID NO:2) His, Phe, Asn, Pro, Arg, Phe, Asn, Glu, Asn, Asn, Arg, Arg, Val, Ile, Val, Cys, Asn, Thr, Lys, Leu, His, Asn, Asn, Trp, Gly, Arg, Glu, Glu, Gln, Arg, Ser, Val, Phe, Pro, Phe, Glu, Ser, Gly, using the hybridoma technique of Kohler and Milstein; see, for example, A. Raz and R. Lotan; Cancer and Metastasis Reviews 6:433 (1987). The monoclonal antibody which belongs to the IgG class was purified by affinity chromatography on Sepharose-protein A (Pharmacia, Uppsala, Sweden).

5. Purification of Antibodies on Sepharose-protein A

Mouse IgG, binds to protein-A at pH 8.0, whereas mouse IgG of other subclasses as well as IgG from polyclonal rabbit-antiserum are bound at pH 7.2. A Sepharose-protein A column (5 ml) was equilibrated with 0.1M sodium-phosphate buffer, pH 7.2 or 8.0, and 1 ml ascitic fluid or 0.5 ml antiserum, diluted with 0.5 ml of the respective buffer, was applied and allowed to react for a period of 30 to 60 minutes. The column was rinsed with the same buffer until baseline absorbance ($A_{280}$) was regained in the effluent. For elution of the IgG fraction from the protein-A column, the pH was then lowered gradually by replacing the phosphate buffer with 0.1M citrate buffers of pH 6, 4.5 and 3.0. The pooled IgG-containing peak was dialyzed against phosphate buffered saline (PBS; 10 mM phosphate, 150 mM NaCl, pH 7.2) and concentrated to 1–2 mg protein/ml over a P10 membrane in an Amicon concentrator. The preparation was stored at −20° C. until use.

6. Pectin Solution

Citrus pectin solution was prepared from Sigma Co. The dry pectin, 73% degree of esterification was dissolved slowly in a strongly stirred 100 ml CMF/PBS.

7. Solid phase Radioimmunoassay for Soluble protein Antigens (a) The assay used was a modification of the principle procedure disclosed by S. K. Pierce and N. R. Klinman; J. Exp. Med. 144:1254 (1976). Blood samples from mice were taken at appropriate times. The blood was clotted in 5 ml tubes. The serum was collected and EDTA 2 mM and PMSF 0.2 mM was added to the serum and frozen. A sample of 50 μl from the serum was tested three times in triplicates according to the modified method of solid phase radioimmuno-assay for soluble protein antigens of Pierce and Klinman referenced above, using the pectin coated plates of the present invention. The coating buffer of the plate was sodium carbonate (50 mM, pH 9.6) containing 0.1 g sodium azide per liter.

After adding 50 ul of serum from blood in each well of the microtitre plate, it was allowed to incubate for 24 hours at 4° C. After removing the serum, the plate was washed once with PBS-BSA 0.05% and flicking the fluid into a sink. Then the well was refilled with PBS-BSA for one hour at room temperature to block the remaining protein-binding sites on the plate. The plate was washed three times and then 200 ul of 100 ng IgG was added to each well and the plate was incubated for four hours. The plate was washed with PBS and the $^{125}$I-anti-rabbit-Fab' was added to the wells for two hours incubation. The plates were dried under a lamp and the wells were cut and counted in a gamma counter.

CBP is present in various murine and human tumor cells as has been discussed above. In this experimental series, tumor cells that are known to have the CBP on their cell membrane and which have the propensity to colonize lungs were used in an experimental metastasis assay to investigate whether there is a direct correlation between serum levels of the galactose receptor of the present invention and lung colonization.

Female BALB/c mice 8 to 12 weeks old were produced in an animal colony, which was established by cesarean derivation of a litter of mice from BALB/cfC3H parents obtained from the Cancer Research laboratory, Berkeley, Calif. At sequential times after injection of tumor cells, groups of mice were sacrificed. If tumor nodules were not grossly visible, lungs were weighed and minced into pieces of approximately 1 mm$^3$ and enzymatically dispersed by the technique described in Experimental Cell Research, 173:109 (1987). Briefly, lungs were presoaked for one hour in 25 ml of an enzyme solution containing 1 mg/ml collagenase type IV (Sigma Chemical Co., St. Louis, Mo.) and 36 units of porcine pancreatic elastase (ICN Biomedicals, Costa Mesa, Calif.) at 4° C. The samples were mechanically dispersed with four sequential, 30 second and three sequential, one minute periods in a Stomacher blender (Tekmar Co., Cincinnati, Ohio). Following each dispersion period, a portion of the cell suspension was removed and an equal volume of DME-10 added. The colonies were fixed with Carnoy's solution, stained with crystal violet, counted and total colony forming cells per organ calculated. Population doubling times were calculated from regression analysis of the increasing number of colony forming cells per organ over time.

In the second experiment, unanesthetized female C57BL/6 mice (eight weeks old) were inoculated (I.V.) in the tail vein with 10$^5$ tumor cells in 0.2 ml of PBS. After 17 days, the mice were autopsied and their lungs were removed, rinsed, and fixed with 5% formaldehyde in PBS. The number of tumor colonies in the lungs were then determined under a dissecting microscope. The results determined by visual inspection were correlated with those from the assay, and the data is summarized in FIGS. 2 and 3.

Results

Figure 2:
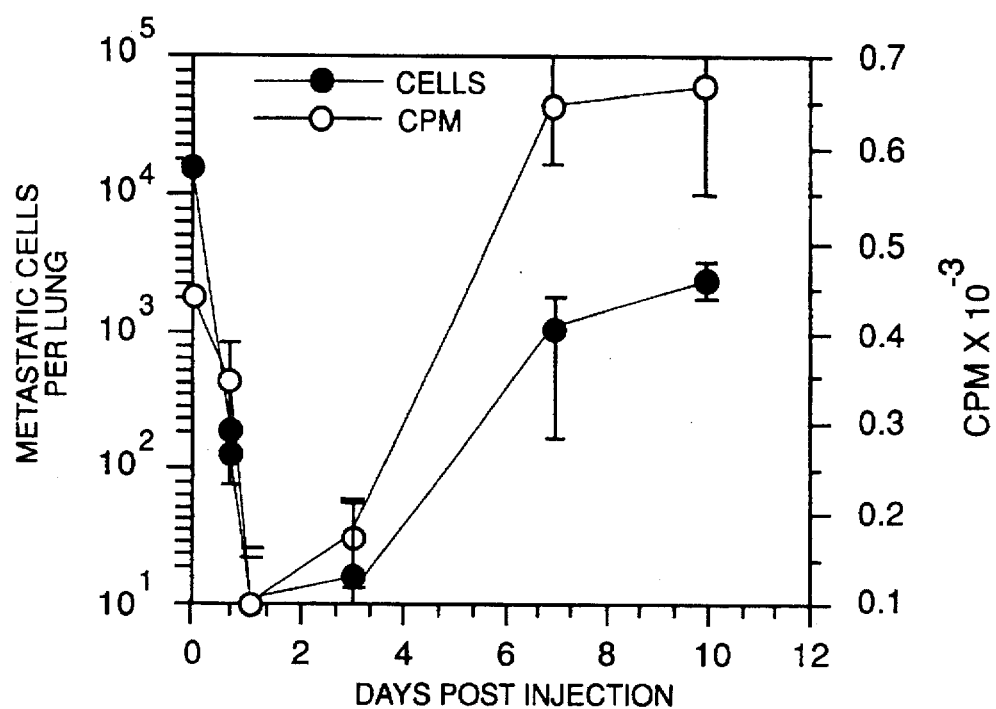
FIG. 2 is a graph showing test results from mice, taken at various days after injection with metastatic cells, illustrating the detection of said cells in accord with the present invention.

Applicant has utilized test plates covered with pectin to examine and correlate the levels of CBP in serum and lung colonization. Two types of experiments were conducted. Both types of analyses revealed a biphasic distribution wherein initially (time 0, immediately after injection) the cells were cleared from the circulation and trapped in the capillary bed of the lungs. After an additional time period, the non-extravasating cells were released from the lungs and detected in the circulation where eventually they perished as indicated at approximately day 1 in FIG. 2. Each point in FIG. 2 represents the median of four to eight mice and P is less than 0.01 by Mann Whitney U test on all days for the 4T07 cells. Simultaneously, the blood serum was collected and the solid phase radioimmuno assay procedure was performed using monoclonal antibodies generated in rabbits against CBP (50 pg/100 ul)/well. A sample of 50 ul of serum was tested three times in triplicate and each of the values of antibody bound corresponded to $^{125}$I counts per minute and represents the average plus or minus the standard error which indicated the amount of the active galactose binding site in the serum.

This is a standard experimental model and under the experimental conditions used, the cells do not produce metastasis at any other organs besides the lungs. Morphological studies of the extravasation of the tumor cells from blood vessels revealed that the time needed to obtain an extravascular position varies and may occur between 2.5 and 72 hours after adhesion to the endothelial layer of the blood capillaries. Fidler, et al.; Adv. Cancer Research, 38:149 (1978).

The second phase of the curves (days 3–10) demonstrates that the successful seeding and proliferation of the tumor colonies into visible metastasis is accompanied by the detection of the CBP in the circulation as indicated in FIG. 2. Therefore, either the tumor metastasis shed viable cells into the circulation or alternatively part of the growing metastatic cells are eliminated by the host-immune system and their residues are then detected in the circulation. Therefore, in accord with the present invention, it has been shown that using a solid phase radioimmuno assay system and pectin coated plates, it is possible to detect the galactose binding receptor of the present invention in serum after the injection of metastatic cells. FIG. 2 shows a high correlation between the amount of the receptor in the blood and the number of metastatic nodules in the lungs, after seven and ten days post injection (r=0.941 and 0.983 respectively).

To generalize the findings with the F4T07 cells, applicant analyzed B16 melanoma systems. B16-F1 cells were injected intravenously and 17 days post injections the blood was drawn from the mice. The mice were then sacrificed and the lungs removed and the number of tumor nodules counted, the data being shown in FIG. 3.

More specifically, $1\times10^5$ cells were injected intravenously. Mice were sacrificed at 17 days post injection and the nodules per lung were measured according to methods set forth above for spontaneous metastasis.

Figure 3:
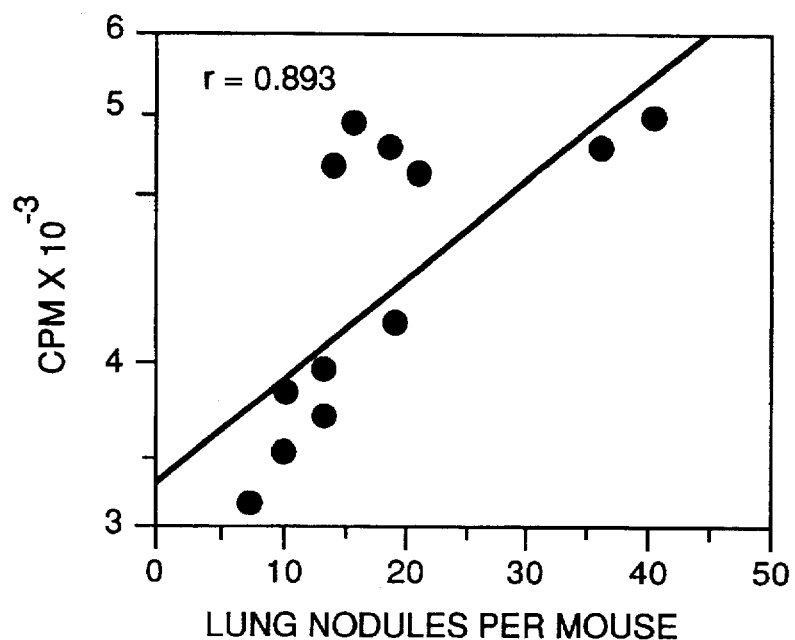
FIG. 3 is another graph depicting the correlation between lung nodules per mouse and the amount of CBP detected in accord with the present invention.

Referring to FIG. 3, each point represents the median of four to eight mice by the Mann Whitney U test (P less than 0.01) on all days for the B16F1 cells. Simultaneously, the blood serum was collected and the solid phase radio immunoassay procedure was performed utilizing the pectin coated plates made in accordance with the present invention and monoclonal antibodies generated in rabbits against the galactose binding site of CBPs (50 pg100 ul) per well. A sample of 50 microliters of serum was tested three times in triplicate and each value of antibody found corresponded to $^{125}I$ counts per minute and represents the average plus or minus the standard error.

The comparison between the number of lung nodules with the serum level of the galactose binding site from each individual mouse is highly correlative wherein r=0.893 as shown in FIG. 3. This data strongly supports the initial observation as presented in FIG. 2.

In view of the above experiments, it is clear that the present invention provides a simplified diagnostic tool for screening and monitoring the existence of metastasizing tumor cells in the circulation thereby allowing detection and monitoring of circulating tumor cells before and after removal of the primary tumor. The present invention makes it possible to detect the efficiency of chemotherapy treatments in eliminating metastatic spread.

In accord with another feature of the present invention, there are provided therapeutic methods for the treatments of metastatic disease, based upon the galactose binding site of the present invention. As shown in the experimental series, metastatic cells express CBPs which include the galactose binding site. The CBPs play a role in cellular interactions leading to the formation of metastatic nodules. In accord with one therapeutic method, a peptide corresponding to the galactose receptor is synthesized and injected into an animal, where it acts as an antigen to trigger the formation of antibodies. Since the peptide which is injected is entirely, or primarily comprised of the active GBP receptor site, it is quite effective in generating antibodies which are highly specific for the galactose binding receptor of CBPs.

These antibodies bind to the surface of circulating tumor cells. The presence of antibodies both inhibits the agglomeration of cells at tissue sites and hence prevents metastasis, and also can mark the cells for destruction by the immune system.

Previously, immunotherapeutic treatments for cancers have been attempted wherein various peptides have been injected into patients to elicit immune responses. These therapies have not been successful. It is believed that this lack of success is a result of the fact that the prior art peptide materials did not generate an effective level of active antibodies. The receptor of the present invention is highly specific and will induce the generation of very active antibodies. Also, in a most preferred form of the present invention, the peptide is administered in conjunction with an immune system adjuvant. The adjuvant intensifies the body's response to the peptide, causing the generation of a very high level of antibodies. While some of these antibodies will attack the administered peptide, the excess will attach to metastatic cells and prevent their aggregation; additionally, the antibodies will mark the metastatic cells for destruction of macrophage and T-cell attack. There are a number of adjuvants well known to those of skill in the art, including Freud's Complete Adjuvant (CFA) and such materials may be used in the practice of the present invention. One adjuvant material having particular utility is that disclosed in co-pending U.S. patent application Ser. No. 08/087,628, the disclosure of which is incorporated herein by reference.

As described, the antibodies may be directly raised in the body of the patient undergoing therapy, in which instance the peptide will function in the manner of a vaccine. In other instances, the antibodies may be generated in another animal and harvested for subsequent use as a therapeutic material. In further embodiments of this particular aspect of the invention, monoclonal technology may be applied to the preparation of the antibodies.

In other embodiments, the principles of the present invention may be applied toward an extracorporeal therapy for removing metastatic cells from the blood stream, based upon the presence of the galactose receptor therein. As described above, the receptor binds to carbohydrates having galactose, or galactose containing polysaccharides therein; similarly, antibodies may be readily developed to the specific galactose receptor. In accord with the present invention, a carbohydrate or antibody which binds the receptor is supported on a plate, column packing, capillary bed or the like and the patient's blood is shunted through the supported material. The tumor cells which include the galactose receptor will bind to the support and be retained. In this manner, these cells which would otherwise metastasize in the body, are removed.

Yet another therapeutic methodology is made possible by the present invention. There is provided an agent which binds to the galactose receptor in vivo. In this therapeutic approach, a relatively high molecular weight material having the ability to bind to the receptor is introduced into a patient's bloodstream. The material recognizes the galactose-binding site on metastatic cells and attaches thereto. This binding interferes with subsequent cell-cell and cell-substrate interactions preventing agglomeration and metastasis. The high molecular weight of the material retards its clearance from the blood.

One particularly preferred material comprises a galactose material bound to a polymer. The polymer should be biocompatible, and it has been found that a molecular weight range of approximately 10 kilodalton will preserve the proper balance between solubility in the bloodstream and retardation of clearance.

Figure 4:
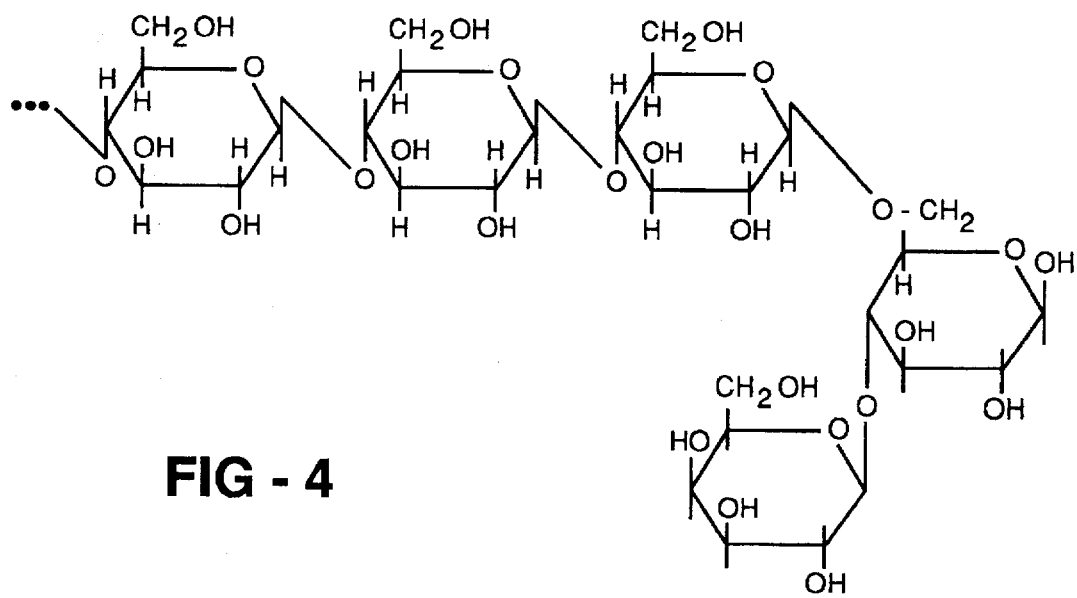
FIG. 4 is a depiction of therapeutic agent, which is structured in accord with the principles of the present invention and which actively binds to CBPs.

Referring now to FIG. 4, there is shown one particular therapeutic material. This material comprises lactose, which is a disaccharide of galactose and glucose, bound to a polymeric chain. As shown, the polymeric chain is a cellulose based polymer such as cellotriose, and as indicated, still further units may be bound to the chain to increase its molecular weight. In the FIG. 4 illustration, the glucose is shown as bound to the polymeric chain by an ether linkage. It is to be understood that coupling may be accomplished via other types of chemical bonds.

Other therapeutic agents may be prepared in accord with the present invention. For example, the polymeric portion of the molecule may be constituted by a variety of other polymers having the requisite biocompatibility and solubility properties. Toward that end, other carbohydrate polymers, peptides and the like may be employed, as well as synthetic polymers. The sugar portion of the agent may, as noted previously, be constituted by galactose, or galactose containing polysaccharides.

The various therapeutic methods of the present invention may be used either singly or in combination with one another, as well as with other therapies. The present invention makes possible a diagnostic system wherein the presence of metastatic cells may be detected in a patient for purposes of diagnosing disease and monitoring the effectiveness of therapies. The invention also provides an immunotherapeutic method and a synthetic therapeutic agent for controlling the actions of metastatic cells in a patient, as well as an extra corporeal therapy for eliminating such cells. All of the foregoing are based upon the identification of a particular galactose receptor which is associated with, and responsible for, the action of the metastatic cells.

It will be appreciated that in view of the disclosure and discussion herein, variations of the therapies and methods described, as well as new therapies and methods, will be readily apparent to one of skill in the art. The foregoing drawings, discussion and examples are merely meant to be illustrative of particular aspects of the present invention, and are not meant to be limitations upon the practice thereof. It is the following claims, including all equivalents, which define the scope of the invention.

I claim:

1. A galactose-specific, carbohydrate binding polypeptide which consists of the amino acid sequence (SEQ ID No:1):

Ile, Val, Cys, Asn, Thr, Lys, Leu, His, Asn, Asn, Trp, Gly, Arg, Glu, Glu, Arg, Gln, Ser, Val, Phe, Pro, Phe, Glu, Ser, Gly.

2. A galactose-specific, carbohydrate binding polypeptide which consists of the amino acid sequence (SEQ ID No:6) His, Phe, Asn, Pro, Phe, Asn, Glu, Asn, Asn, Arg, Arg, Val, in which the Val is joined to the Ile of the amino acid sequence (SEQ ID No:1) Ile, Val, Cys, Asn, Thr, Lys, Leu, His, Asn, Asn, Trp, Gly, Arg, Glu, Glu, Arg, Gln, Ser, Val, Phe, Pro, Phe, Glu, Ser, Gly.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
( A ) LENGTH: 25 amino acids
( B ) TYPE: amino acid
( C ) STRANDEDNESS: Not Relevant
( D ) TOPOLOGY: Not Relevant ( x i ) SEQUENCE DESCRIPTION: SEQ ID NO:1:

Ile Val Cys Asn Thr Lys Leu His Asn Asn Trp Gly Arg Glu Glu Arg
1               5                   10                  15

Gln Ser Val Phe Pro Phe Glu Ser Gly
            20                  25

( 2 ) INFORMATION FOR SEQ ID NO:2:

( i ) SEQUENCE CHARACTERISTICS:
( A ) LENGTH: 38 amino acids
( B ) TYPE: amino acid
( C ) STRANDEDNESS: Not Relevant
( D ) TOPOLOGY: Not Relevant ( x i ) SEQUENCE DESCRIPTION: SEQ ID NO:2:

His Phe Asn Pro Arg Phe Asn Glu Asn Asn Arg Arg Val Ile Val Cys
1               5                   10                  15

Asn Thr Lys Leu His Asn Asn Trp Gly Arg Glu Glu Arg Gln Ser Val
            20                  25                  30

Phe Pro Phe Glu Ser Gly
            35

( 2 ) INFORMATION FOR SEQ ID NO:3:

( i ) SEQUENCE CHARACTERISTICS:
( A ) LENGTH: 6 amino acids
( B ) TYPE: amino acid
( C ) STRANDEDNESS: Not Relevant
( D ) TOPOLOGY: Not Relevant (x i) SEQUENCE DESCRIPTION: SEQ ID NO:3:

```
Ile Val Cys Asn Thr Lys
1               5
```

(2) INFORMATION FOR SEQ ID NO:4:

(i) SEQUENCE CHARACTERISTICS:
      (A) LENGTH: 4 amino acids
      (B) TYPE: amino acid
      (C) STRANDEDNESS: Not Relevant
      (D) TOPOLOGY: Not Relevant (x i) SEQUENCE DESCRIPTION: SEQ ID NO:4:

```
Val Phe Pro Phe
1
```

(2) INFORMATION FOR SEQ ID NO:5:

(i) SEQUENCE CHARACTERISTICS:
      (A) LENGTH: 6 amino acids
      (B) TYPE: amino acid
      (C) STRANDEDNESS: Not Relevant
      (D) TOPOLOGY: Not Relevant (x i) SEQUENCE DESCRIPTION: SEQ ID NO:5:

```
Trp Gly Arg Glu Glu Arg
1               5
```

(2) INFORMATION FOR SEQ ID NO:6:

(i) SEQUENCE CHARACTERISTICS:
      (A) LENGTH: 13 amino acids
      (B) TYPE: amino acid
      (C) STRANDEDNESS: Not Relevant
      (D) TOPOLOGY: Not Relevant (x i) SEQUENCE DESCRIPTION: SEQ ID NO:6:

```
His Phe Asn Pro Arg Phe Asn Glu Asn Asn Arg Arg Val
1               5                   10
```